(12) United States Patent
Melles

(10) Patent No.: US 7,618,619 B2
(45) Date of Patent: *Nov. 17, 2009

(54) COLORED VISCO-ELASTIC COMPOSITION

(75) Inventor: Gerrit Reinold Jacob Melles, Rotterdam (NL)

(73) Assignee: Medical Technology Transfer Holding B.V., Rotterdam (NL)

( * ) Notice: Subject to any disclaimer, the term of this patent is extended or adjusted under 35 U.S.C. 154(b) by 433 days.

This patent is subject to a terminal disclaimer.

(21) Appl. No.: 10/236,661

(22) Filed: Sep. 6, 2002

(65) Prior Publication Data

US 2003/0088233 A1    May 8, 2003

Related U.S. Application Data

(63) Continuation of application No. PCT/NL01/00188, filed on Mar. 7, 2001.

(51) Int. Cl.
*A61K 31/74* (2006.01)
(52) U.S. Cl. .................................... 424/78.04
(58) Field of Classification Search ............... 424/78.04
See application file for complete search history.

(56) References Cited

U.S. PATENT DOCUMENTS

| 4,113,505 | A | * | 9/1978 | Bellanca et al. .......... 106/124.1 |
| 4,350,676 | A | | 9/1982 | Laties et al. |
| 4,666,699 | A | | 5/1987 | Slifkin |
| 4,778,825 | A | | 10/1988 | Smith et al. |
| 5,061,696 | A | * | 10/1991 | York ........................... 514/54 |
| 5,273,751 | A | * | 12/1993 | Dubroff ...................... 424/427 |
| 5,569,191 | A | | 10/1996 | Meyer |
| 5,792,103 | A | * | 8/1998 | Schwartz et al. .............. 604/82 |
| 6,024,719 | A | | 2/2000 | Morris |
| 6,186,148 | B1 | | 2/2001 | Okada |
| 6,367,480 | B1 | | 4/2002 | Coroneo |
| 6,372,449 | B1 | | 4/2002 | Coroneo |
| 6,533,769 | B2 | | 3/2003 | Holmen |
| 6,696,430 | B1 | * | 2/2004 | Melles ........................ 514/150 |
| 6,720,314 | B1 | * | 4/2004 | Melles ........................ 514/150 |

FOREIGN PATENT DOCUMENTS

| EP | 98201542 | * | 5/1998 |
| EP | 98202751 | * | 8/1998 |
| EP | 0 974 320 | | 1/2000 |
| EP | 0974320 | * | 1/2000 |
| GB | 2204238 | * | 10/1988 |
| GB | 2 204 238 | | 11/1998 |
| WO | WO 86 02548 | | 5/1986 |
| WO | WO 8602548 | * | 5/1986 |
| WO | PCT/NL99/00284 | * | 5/1999 |
| WO | WO 99/58160 | * | 11/1999 |

OTHER PUBLICATIONS

Atmaca et al., "La detection des neovaisseaux sous-retiniens au moyen de la video-angiographie au vert d'indocyanine," (with English abstract) J. Fr. Ophthalmol, 1997, pp. 189-194, vol. 20.

Black, H., Soft-shell technique uses two kinds of viscoelastics to achieve good results, Ocular Surgery News, Sep. 15, 1996, p. 17.

Budavari, S., The Merck Index, 1996, p. 1668, Whitehouse Station, NJ, Merck & Co., Inc.

Gimbel, "Development, advantages, and methods of the continuous circular capsulorhexis technique," J. Cataract Refract Surg., 1996, pp. 31-37, vol. 16.

Hoffer, K.J., McFarland J.E., Intracameral Subcapsular Flourescein Staining for Improved Visualization During Capsulorhexis in Mature Cataracts, J Cataract Refract Surg., Jul. 1993, p. 566, vol. 19.

Horiguchi, Arch Ophthalmol, 1998, pp. 535-537, vol. 116.

Liu, "Trypan Blue Staining on Retinal Ganglion Cell of Rat Insulted in Experimental High Intraocular Pressure," 1992, p. 1030, abstract, No. XP-002082879, Department of Neurobiology, University Changsha, Hunan, China.

Melles, Gerrit R.J., Trypan blue capsule staining to visualize the capsulorhexis in cataract surgery, "Techniques," Jan. 1999, pp. 7-9, vol. 25.

Norn, "Per Operative Trypan Blue Vital Staining of Corneal Endothelium," Acta Ophthalmologica, 1980, pp. 550-555, vol. 58.

Norn, "Vital Staining of Corneal Endothelium in Cataract Extraction," Acta Ophthalmologica, 1971, pp. 725-733, vol. 49.

Saito, "Vital Staining of Retina and Uvea with Trypan Blue," (with English abstract) 1979, pp. 41-50, Department of Ophthalmology, Jikei University School of Medicine, Tokyo, Japan.

(Continued)

*Primary Examiner*—Carlos A. Azpuru

(57) ABSTRACT

The invention relates to a visco-elastic composition for use in ocular surgery and to a method of using said composition. Specifically, the present visco-elastic composition comprises a visco-elastic substance and at least one vital dye. The invention enables a visual distinction of the visco-elastic composition from the surrounding aqueous or intraocular structures during ocular surgery, so that the amount present within the eye, the location and the effects of the visco-elastic material can be better monitored.

8 Claims, No Drawings

OTHER PUBLICATIONS

Schmidt, "Ultrastructure of Trypan Blue Induced Ocular Defects: I. Retina and Lens," Teratology, 1983, pp. 131-144, vol. 28.

Spector, "A Brief Photochemically Induced Oxidative Insult Causes Irreversible Lens Damage and Cataract I. Transparency and Epithelial Cell Layer," 1995, pp. 471-481.

Solomon, "Protective Effect of the Anterior Lens Capsule during Extracapsular Cataract Extraction," Ophthalmology, 1989, pp. 591-597, vol. 96(5).

Sulzer, Alcian blue and neutral red staining of retinal synaptic layers, J Histochem Cytochem, pp. 1513-1515, vol. 34(5), (1986).

Taniuchi, "Intraocular Penetration of Trypan Blue and of Colloidal Carbon Administered by IntraTenon's Capsulary Injection," (with English abstract) Folia Ophthalmol, 1981, pp. 343-350, vol. 32, Department of Ophthalmology, Jikei University School of Medicine, Tokyo, Japan.

Caplus abstract, (English abstract) Vital staining of ocular tissue by injecting trypan blue into the anterior chamber, Liu et al., 1981, pp. 1630-1637, vol. 32(7), Nippon. Ganka Kiyo.

Dorland's Medical Dictionary, 1992, p. 1455, 27th Edition.

Medline Acc No. 72009521, The fine structure of the inner limiting membrane of the rat retina as revealed by ruthenium red staining, Journal of Ultrastructure Research, Matsusaka, 1971, pp. 312-317, vol. 36(3).

* cited by examiner

COLORED VISCO-ELASTIC COMPOSITION

RELATED APPLICATIONS

This application is a continuation of PCT Patent Application number PCT/NL01/00188, designating the United States and filed Mar. 7, 2001; which claims the benefit of the filing date of European Patent Application number 00200811.8, filed Mar. 7, 2000; each of which is hereby incorporated herein by reference in its entirety for all purposes.

The invention relates to a visco-elastic composition for use in ocular surgery and to a method of using said composition.

Visco-elastic compositions, i.e. transparent viscous compositions that are well tolerated following brief exposure to intraocular structures, are used in various types of ocular surgery. They are used as a surgical aid to protect, or even seal from its surroundings, intraocular tissues (for example the corneal endothelium during phacoemulsification), as a space maintainer (for example to maintain the anterior chamber of the eye), and to facilitate intraocular maneuvers (for example to make a controlled capsulorhexis).

Various types of visco-elastic compositions are currently used, having different biochemical compositions, viscosities, rheologic properties, and/or dispersive or adhesive properties. The properties of the composition vary with the biochemical composition, to meet the needs for each type of surgery. Visco-elastic compositions that are currently used in ophthalmology contain a viscous or a viscoelastomeric composition such as hyaluronic acid, alginic acid, polymannuronic acid, to name but a few examples.

Currently available visco-elastic compositions are completely transparent, so that the material does not interfere with the visualization of intraocular structures and surgical instruments during surgery. A disadvantage of the transparency of the material is that it may be difficult to determine its intraocular presence, amount and location. For example, it is of great importance that at the end of surgery all of the visco-elastic composition is removed from the eye to prevent intraocular pressure elevation after surgery. Due to the transparency of the material it may be difficult to judge if no residual visco-elastic composition is left in the eye. In general, the higher the viscosity of the visco-elastic composition, the greater the risk of postoperative complications like pressure elevation. Complete removal of a visco-elastic composition may in particular be important in elective ocular surgery, for example refractive surgery, in which healthy eyes with perfect visual acuity are operated, and complications resulting from the use of a visco-elastic are unacceptable.

Poor visibility of a visco-elastic composition within the eye also prohibits exact visualization of the amount injected and the effects of the material. For example, it can not be determined to what extent intraocular structures are displaced, disrupted, pressurized, or damaged by injecting a visco-elastic composition in or near intraocular tissues.

For example, in the event of a posterior capsule tear in complicated cataract surgery, it may be difficult to distinguish the corpus vitreum from any residual or purposely injected visco-elastic material. Furthermore, the transparency of the visco-elastic composition may prohibit visualization of the composition after surgery, in the event remnants of it are, purposely or not, left behind in the eye at the end of the surgery.

It has been proposed to formulate a visco-elastic material containing fluorescein as a dye in the past. These materials, however, did not have the desired advantages in ocular surgery. Dyes like fluorescein are capable of diffusing out of the visco-elastic composition as a result of which they also color the surrounding tissue.

The international patent application 86/02548 discloses a composition for ophthalmic use containing an aqueous solution of a high molecular polymer to a polymeric dye has been added. It is stated that, in order to avoid the diffusion problems of fluorescein and to maintain the dye clear in the composition, it is necessary for the polymeric dye to have a molecular weight exceeding 10,000, preferably exceeding 30,000, more preferably as high as possible without affecting its solubility in water. The polymeric dyes used are chosen from the group known as "reactive dyes".

This invention aims to overcome the above described problems associated with poor visibility of visco-elastic material during ocular surgery. It is an object of the invention to enable a visual distinction of a visco-elastic composition from the surrounding aqueous or intraocular structures, so that the amount present within the eye, the localization and the effects of the visco-elastic material can be better monitored during surgery. It is a further object of the invention that said visual distinction is enabled without the use of a polymeric dye.

Surprisingly, it has now been found that said object may be attained by using a visco-elastic composition comprising a specific dye or mixture of dyes. Hence, the invention relates to a visco-elastic composition comprising at least one visco-elastic substance and at least one vital dye, which dye substantially does not diffuse out of the visco-elastic composition. The vital dye that is used according to the invention is non-polymeric and has a molecular weight below 2,000 D, preferably below 1,000 D.

The stained visco-elastic composition can be used in two ways. First, when a relatively low concentration of the dye(s) is used to lightly stain the composition, the transparency of the visco-elastic material is maintained to a certain extent, so that surgical maneuvers can be performed above, aside of, within, or underneath the level at which the composition is present within the eye (relative to the surgical view).

Second, when a relatively high concentration of the dye(s) is used to densely stain the composition, the visco-elastic properties but not the transparency of the composition are maintained, so that surgical maneuvers can be performed above or aside of the level at which the composition is present within the eye (relative to the surgical view).

For the first manner of using the present composition mentioned above, by using a visco-elastic composition according to the invention, a clear visibility of the visco-elastic composition is attained, by which is meant that a clear distinction can be observed between the visco-elastic composition and surrounding intraocular structures during use in ocular surgery. Particularly, the intraocular structures surrounding the site at which the visco-elastic composition is employed are not noticeably stained, not even during surgery. This distinction facilitates the controlled use of the visco-elastic composition, reduces the risk of under- or overfilling the anterior chamber, inadvertent disruption, pressurization or damage to the intraocular structures, and facilitates complete removal of all visco-elastic material from the eye at the end of surgery.

For the second manner of using the present composition as mentioned above, by using the visco-elastic composition according to the invention, again a clear visibility of the visco-elastic composition is attained, but the ocular tissue structures underlying the composition (relative to the surgical view) are purposely obscured. This distinction facilitates the controlled use of the composition, improves the visualization of structures overlying the composition, enables controlled displacement or stabilization of intraocular structures, facilitates complete removal of the composition at the end of the surgery, or visualization of the composition after surgery in the event that the composition was purposely left in the eye at the end of the surgery.

It has been observed that the use of the present visco-elastic composition in ocular applications does not have a detrimental effect on the tissue with which the visco-elastic composition is contacted. Furthermore, it has been observed that shortly after the surgical procedure has been completed, substantially all visible traces of the composition, and thus of the dye, have disappeared. Without wishing to be bound by theory, it is believed that the dye shows a significantly stronger interaction with the visco-elastic substance in the composition than with the tissues and structures of the ocular area. It has surprisingly been found that the dye that is used in accordance with the invention, when used in a visco-elastic composition, does not stain intraocular structures, while the same dye does stain intraocular structures when it is used in an aqueous or salt solution. Thus, a patient undergoing a surgical procedure involving the use of a visco-elastic composition in accordance with the invention experiences no more distress or undesired side effects as when a conventional surgical procedure is employed. Furthermore, undesired staining of the intraocular structures does essentially not, or not to an adverse extent, occur.

In addition it has been found that the presence of at least one vital dye in a visco-elastic composition according to the invention does substantially not interfere with the properties that the visco-elastic substance provides to the composition. In practice, a visco-elastic composition is, amongst others, selected for its optimal viscosity. The viscosity should be high enough to achieve a suitable sealing of the site of application; and it should be low enough to allow for an easy removal after surgery.

A first component of a visco-elastic composition according to the invention is a visco-elastic substance. This substance will be selected for its visco-elastic and rheological properties, dependent on the circumstances under which it is intended to be used. Furthermore, the visco-elastic substance must have the capacity of giving the envisaged properties to the composition in concentrations that are physiologically and toxicologically acceptable. In other words, the minimum amount of visco-elastic substance required should so be low that no, or hardly any, adverse toxic effects occur in the eye. Of course, the amount in which the visco-elastic substance will be incorporated into the composition will also depend on the desired visco-elastic and rheological properties of the composition.

Suitable examples of visco-elastic substances that can be employed are glycosaminoglycans, such as hyaluronic acid and salts thereof; chondroitin sulfate, alginic acid, polymannuronic acid, polyglucuronic acid and other polyglycuronic acids, mucopolysaccharides, polynucleic acids, polynucleosides, polynucleotides, polydeoxynucleic acids, polydeoxynucleosides, polydeoxynucleotides, polyamino acids, collagen and modified collagen, modified cellulose such as: methylcellulose, hydroxyethylcellulose, hydroxypropyl-cellulose and hydroxypropylmethylcellulose, polyvinyl pyrrolidone, polyvinyl alcohol, polyethyleneimine, polyhydroxyethyl methacrylate and other acrylic or methacrylic acid polymers, and the like, in a physiologically compatible solution designed to minimize the traumatic effects of surgery at the cellular level. This invention also relates to methods for conducting surgery, especially ocular surgery, which comprise administration of such compositions. The foregoing "equivalents" of hyaluronic acid are not publicly known, and constitute distinct embodiments of the present invention.

Hyaluronic acid is a preferred visco-elastic substance. It is a naturally occurring high viscosity glycosaminoglycan having alternatintg b 1-4 glucosaminidic bonds. The molecular weight of this material is generally within the range of 50,000 to 8,000,000, although there are reports of molecular weights as high as 13,000,000 depending on the source, method of isolation and method of determination.

The zero shear viscosity of this visco-elastic substance generally varies from 50,000 to 10,000,000 centipoise.

A preferred composition according to the invention will contain about 0.1 to 5.0 weight percent of hyaluronic acid (molecular weight from about $0.7 \times 10^6$) as the sodium, potassium or ammonium salt, in the following salt solution:

| Component | Amount (wt. %) |
|---|---|
| Sodium Chloride | 0.01 to 1.0 |
| Potassium Chloride | 0.01 to 1.0 |
| Dried Sodium Phosphate | 0.01 to 1.0 |
| Calcium Chloride | 0.01 to 1.0 |
| Magnesium Chloride | 0.01 to 1.0 |
| Dextrose | 0.01 to 1.0 |
| Glutathione (—SH or —S—S—) | 0.005 to 0.5 |
| Sodium Bicarbonate | 0.01 to 1.0 |
| Sodium Hydroxide or Hydrochloric Acid | To Adjust pH |
| Purified Water | QS |
| Osmolality | 200-6-mOsm/kg |
| pH | 5.5-8.5 |

Other preferred compositions are prepared using the previously disclosed viscous or viscoelastic substances, alone or in combination, in place of the hyaluronic acid component.

Hydroxy-propyl-methyl-cellulose, another preferred and visco-elastic substance for the composition of the present invention, generally has a molecular weight in the range of 50,000 to 150,000 (Dalton), and a zero shear viscosity of 3000 to 12,000 (centipoise). A preferred composition according to the invention will contain about 0.1 to 5.0 weight percent hydroxypropyl methylcellulose (HPMC) in the following salt solution:

| 1 ml visco-elastic HPMC contains | |
|---|---|
| HPMC | 20 mg |
| NaCl | 6.4 mg |
| KCl | 0.75 mg |
| CaCl | 0.48 mg |
| MgCl | 0.30 mg |
| Natriumacetate | 3.90 mg |
| Natriumcitrate | 1.70 mg |
| HCl or NaOH to control the pH to | 5.5-8.5 |
| water | QS |

As has been mentioned above, a visco-elastic composition according to the invention comprises a vital dye or a mixture of vital dyes. An important aspect of the invention is that a dye is used which is capable of staining the composition in which it is incorporated without diffusing out of said composition. In other words, a selective staining is achieved. This property of the dye ensures that the surrounding tissues or ocular structures are not stained during surgery.

Suitable dyes having this characteristic further should have sufficient coloring, or staining capacity at concentrations which are physiologically and toxicologically acceptable. In other words, the minimum amount of dye which is necessary to provide sufficient staining for a useful coloring to be visible should so be low that no, or hardly any, adverse toxic effects occur. Preferably, the dye is not or hardly toxic to intraocular tissues, such as the corneal endothelium, the germinative lens cells, and the retinal cell layers. It is further preferred, that substantially no traces of the dye are present in the eye, shortly after the surgical procedure has been completed. As a result, there is hardly any risk of the patient experiencing any side effects from the dye itself.

Particularly good results have been achieved using a dye having the formula (I)

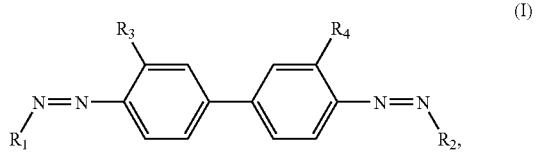

wherein $R_1$ and $R_2$ are the same or different arylgroups, and wherein $R_3$ and $R_4$ are independently chosen from hydrogen, methyl, ethyl, methoxy, amino, hydroxyl, and sulfonate. $R_1$ and $R_2$ are preferably the same and formed by substituted naphtylgroups. Preferably, the naphtylgroups are substituted with one or more of sulfonate groups, amino groups and hydroxyl groups.

In a highly preferred embodiment, the dye is chosen from the group of non-polymeric dyes, such as trypan blue, trypan red, indocyanine green, brilliant crysyl blue, azophloxin, basic blue (Nile blue sulphate), Bismarck brown, basic red (rhodamine 6G), bengal red, eosin, gentian violet, methylene blue, methylene green, Janus green, neutral red, crystal violet.

It has been found that these dyes provide a clearly visible staining at very low amounts. Their molecular weights are well below 10,000. Also, they have an extremely advantageous toxicity profile. In a preferred embodiment, a dye is used which is capable of staining tissue without diffusing through said tissue. More preferably, the dye is trypan blue, methylene blue, gentian violet, or indocyanine green.

Dyes which are preferred according to the invention do not diffuse out of the visco-elastic composition and substantially do not color surrounding tissue structures. This is an important aspect, as diffusion of the dye to surrounding tissue during surgery may be very confusing and may even lead to mistakes. Generally, a surgeon will have a tendency to remove all colored tissue. Thus, by selecting a dye along the guidelines of the invention reduces the risk of undesired removal of tissue. Furthermore, dyes which are preferred according to the invention have a stable and easily distinguishable color intensity, which facilitates their observation and storage. In addition, different intensities of coloration achieved with the preferred dyes are much easier to distinguish from one another as compared to other dyes.

Of course it is also possible to use mixtures of the above dyes as long as the resulting mixture is capable of achieving a color of the visco-elastic composition which can be easily distinguished from the color of the material in the eye at the site of application.

When staining without loss of transparency of the visco-elastic composition is desired, the composition preferably comprises between 0.0005 and 0.01 wt. %, more preferably between 0.005 and 0.002 wt. %, based on the weight of the composition, of the at least one vital dye. When relative dense of the composition is desired (with loss of its transparency), the composition preferably comprises between 0.01 and 1 wt. %, more preferably between 0.02 and 0.3 wt. %, based on the weight of the composition, of the at least one vital dye. In view of the relatively low concentrations involved, it may be useful to use a calorimetric analysis as a measure for the concentration of the vital dye.

The present composition may be in the form of a single solution (or colloidal gel), two solutions which are combined prior to use, or as products wherein the visco-elastic substance, or its equivalent, is present as a hyophilized solid which is solubilized by companion solutions prior to use. The composition is preferably in the form of a physiologically compatible solution. In a particularly preferred embodiment, the composition is formulated as a salt solution, which is isotonic with ocular fluid.

The salt is preferably sodium chloride, sodium phosphate, potassium chloride, calcium chloride, magnesium chloride, or a combination thereof. Suitable examples are Balanced salt solution or Hartmann's lactated Ringer's solution (Nuijts R M M A, Edelhauser H F, Holley G P, "Intraocular irrigating solutions: a comparison of Hartmann's lactated Ringer's solution, BSS and BSS plus", Clin. Exp. Ophtamol., vol. 233 (1995), pp. 655-661). In accordance with this embodiment, the salt concentration will be in the range of 0.8 to 1.0 wt. %, based on the weight of the solution.

It is further preferred that the solution has a neutral pH, i.e. a pH between 6.5 and 7.5. The skilled person will be able to select a suitable buffer, which has the properties to be of use in opthtalmic applications. An example of a suitable buffer is phosphate buffered NaCl, commercially available at NPBI, Emmer-Compascuum, The Netherlands.

The invention further relates to the use of a visco-elastic composition as described above in ocular surgery. Representative, but not restrictive examples are the following. In all types of intraocular surgery, the visco-elastic composition may be used to visualize the location and the amount injected of the composition into the anterior or posterior segment of the eye during surgery, and to facilitate complete removal of all composition at the end of the surgery. In refractive surgery, the composition may be used to prevent overfilling of the anterior chamber during intraocular lens implantation. In cataract surgery, the composition may be used for hydrodissection and hydrodelneation of the lens. In corneal surgery, the composition may be used for controlled dissection and displacement of the various layers of the cornea. In glaucoma surgery, the composition may be used to visualize the flow through the Schlemm Canal, vessels, and filtering bleb. In posterior segment surgery, the composition may be used for controlled dissection, displacement or stabilization of the vitreous, retina, retinal pigment epithelium, or choroid.

Furthermore, more than one visco-elastic composition with varying colors and viscosities, may be used in the same or different ocular compartments during surgery. Representative but not restrictive examples are the following. In cataract surgery, one composition, relatively densely stained and with low viscosity, may be used for hydrodissection of the lens, while the anterior chamber of the eye is maintained with a composition that is relatively lightly stained and has a relatively high viscosity. In glaucoma surgery, one composition, relatively densely stained and with low viscosity, may be used for viscocanalostomy of Schlemm's Canal, while the anterior chamber of the eye is maintained with a composition that is relatively lightly stained and is a relatively high viscosity.

In retinal detachment surgery, one composition, relatively densely stained and with high viscosity, may be used for dissection of the subretinal space (in between retina and choroid) or suprachoroidal space (in between choroid and sclera), while the vitreous cavity is filled with a composition that is relatively lightly stained and also has a relatively high viscosity.

The invention claimed is:

1. A method of performing intraocular surgery, refractive surgery, cataract surgery, coreal surgery, glaucoma surgery, posterior segment surgery, or retinal detachment surgery comprising the application of a composition to a human eye or a part thereof wherein the composition comprises at least one visco-elastic substance and at least one vital dye, which dye substantially does not diffuse out of the visco-elastic composition, and wherein the dye has a molecular weight below 2,000 D and is represented by formula (I)

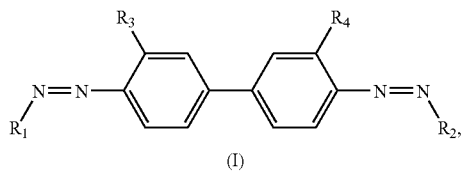

wherein $R_1$ and $R_2$ are the same or different aryl groups, and wherein $R_3$ and $R_4$ are independently chosen from hydrogen, methyl, ethyl, methoxy, amino, hydroxyl, and sulfonate.

2. The method of claim 1, wherein the visco-elastic substance is hyaluronic acid or hydroxypropyl methylcellulose.

3. The method of claim 1, wherein $R_1$ and $R_2$ are the same and formed by naphthyl groups substituted with one or more of sulfonate groups, amino groups and hydroxyl groups.

4. A method of performing intraocular surgery, refractive surgery, cataract surgery, coreal surgery, glaucoma surgery, posterior segment surgery, or retinal detachment surgery comprising the application of a composition to a human eye or a part thereof wherein the composition comprises at least one visco-elastic substance and trypan blue, wherein the trypan blue substantially does not diffuse out of the visco-elastic composition, and wherein the trypan blue is capable of staining tissue substantially without diffusing through said tissue.

5. The method of claim 1, wherein the composition has the form of a physiologically compatible solution or colloidal gel.

6. The method of claim 1, wherein at least one vital dye is present in a concentration between 0.0005 and 0.01 wt. %, based on the weight of the composition.

7. The method of claim 1, wherein at least one vital dye is present in a concentration between 0.01 and 1 wt. %, based on the weight of the composition.

8. The method of claim 1, wherein the composition further comprises between 0.8 and 1.0 wt. %, based on the weight of the solution, of a salt.

* * * * *

UNITED STATES PATENT AND TRADEMARK OFFICE
CERTIFICATE OF CORRECTION

PATENT NO. : 7,618,619 B2 Page 1 of 1
APPLICATION NO. : 10/236661
DATED : November 17, 2009
INVENTOR(S) : Gerrit Reinold Jacob Melles It is certified that error appears in the above-identified patent and that said Letters Patent is hereby corrected as shown below:

Title Page, insert

-- (30)  Foreign Application Priority Data
    March 7, 2000 (EP).....................00200811.8 --.

Signed and Sealed this

Twenty-second Day of December, 2009

David J. Kappos
*Director of the United States Patent and Trademark Office*